United States Patent
Nitzan

[11] Patent Number: 5,811,204
[45] Date of Patent: *Sep. 22, 1998

[54] FLEXIBLE THIN LAYER OPEN ELECTROCHEMICAL CELL

[75] Inventor: Zvi Nitzan, Petah Tikva, Israel

[73] Assignee: Baruch Levanon, Raanana, Israel

[*] Notice: The term of this patent shall not extend beyond the expiration date of Pat. No. 5,652,043.

[21] Appl. No.: 831,379

[22] Filed: Apr. 1, 1997

Related U.S. Application Data

[63] Continuation of Ser. No. 575,190, Dec. 20, 1995, Pat. No. 5,652,043.

[51] Int. Cl.$^6$ .................................................... H01M 6/00
[52] U.S. Cl. ...................... 429/127; 429/82; 429/152; 429/162; 429/224; 429/229; 428/209; 428/210; 428/688; 428/701
[58] Field of Search ...................... 429/152, 127, 429/82, 162, 224, 229; 428/209, 210, 688, 701, 901

[56] References Cited

U.S. PATENT DOCUMENTS

| | | | |
|---|---|---|---|
| 641,335 | 1/1900 | Schmidt . | |
| 2,798,896 | 7/1957 | Bly | 136/181 |
| 3,023,259 | 2/1962 | Coler et al. | 136/6 |
| 3,353,999 | 11/1967 | Osborn | 136/83 |
| 3,375,136 | 3/1968 | Biggar | 136/6 |
| 3,379,574 | 4/1968 | Grulke et al. | 136/90 |
| 3,871,921 | 3/1975 | Beatty et al. | 136/111 |
| 3,901,732 | 8/1975 | Kis et al. | 136/111 |
| 3,969,148 | 7/1976 | Trattner | 136/173 |
| 4,037,026 | 7/1977 | Mabuchi | 429/100 |
| 4,080,728 | 3/1978 | Buckler | 29/623.4 |
| 4,105,815 | 8/1978 | Buckler | 429/152 |
| 4,119,770 | 10/1978 | Land | 429/152 |
| 4,195,121 | 3/1980 | Peterson | 429/127 |
| 4,294,898 | 10/1981 | Hartstein | 429/104 |
| 4,371,593 | 2/1983 | Ramey | 429/97 |
| 4,493,880 | 1/1985 | Lund | 429/97 |
| 4,505,996 | 3/1985 | Simonton | 429/162 |
| 4,614,695 | 9/1986 | Ibbott | 429/127 |
| 4,623,598 | 11/1986 | Waki et al. | 429/162 |
| 4,703,754 | 11/1987 | Ibbott | 128/383 |
| 4,749,875 | 6/1988 | Hara | 307/150 |
| 4,816,354 | 3/1989 | Tamminen | 429/162 |
| 5,014,946 | 5/1991 | Gruber | 248/206.5 |
| 5,019,467 | 5/1991 | Fujiwara | 429/127 |
| 5,035,965 | 7/1991 | Sangyoji et al. | 429/124 |
| 5,102,753 | 4/1992 | Rossoll et al. | 429/192 |
| 5,147,985 | 9/1992 | DuBrucq | 174/260 |
| 5,149,602 | 9/1992 | Savovoc et al. | 429/96 |
| 5,156,932 | 10/1992 | Dougherty et al. | 429/160 |
| 5,180,645 | 1/1993 | More | 429/127 |
| 5,203,709 | 4/1993 | Huang | 439/38 |
| 5,208,121 | 5/1993 | Yahnke et al. | 429/162 |
| 5,254,414 | 10/1993 | Tsenter | 429/29 |
| 5,326,652 | 7/1994 | Lake | 429/127 |
| 5,350,645 | 9/1994 | Lake et al. | 429/124 |
| 5,411,592 | 5/1995 | Ovshinsky et al. | 118/718 |
| 5,432,027 | 7/1995 | Tuttle et al. | 429/127 |

*Primary Examiner*—Bruce F. Bell
*Attorney, Agent, or Firm*—Mark M. Friedman

[57] ABSTRACT

A flexible thin layer open liquid state electrochemical cell which can be used as a primary or rechargeable power supply for various miniaturized and portable electrically powered devices of compact design. The cell includes a wet electrolyte, yet maintains a flexible, thin and open configuration, thus devoid of accumulation of gases upon storage. The cell comprising a first layer of insoluble negative pole, a second layer of insoluble positive pole and a third layer of aqueous electrolyte, the third layer being disposed between the first and second layers and including a deliquescent material for keeping the open cell wet at all times; an electroactive soluble material for obtaining required ionic conductivity; and, a watersoluble polymer for obtaining a required viscosity for adhering the first and second layers to the third layer. The electrochemical cell of the present invention is preferably produced using a suitable printing technology.

30 Claims, 3 Drawing Sheets

FIG. 1
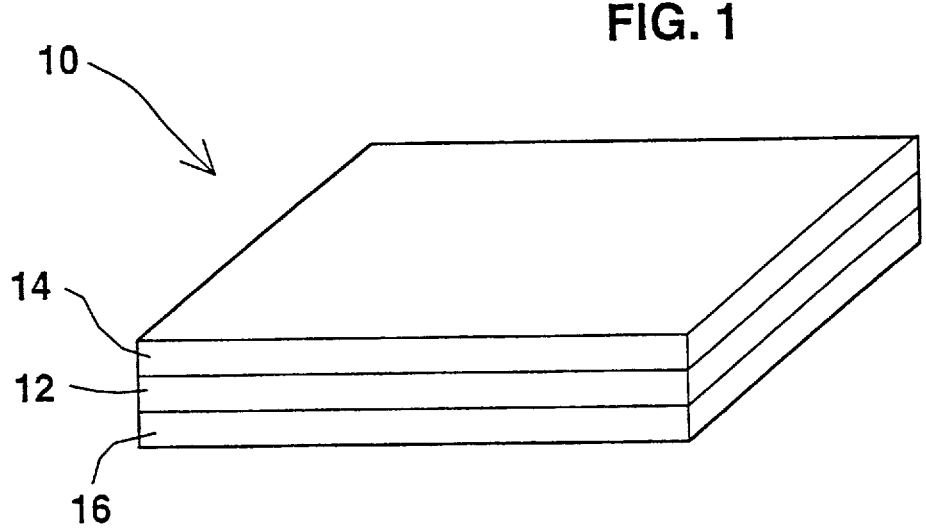
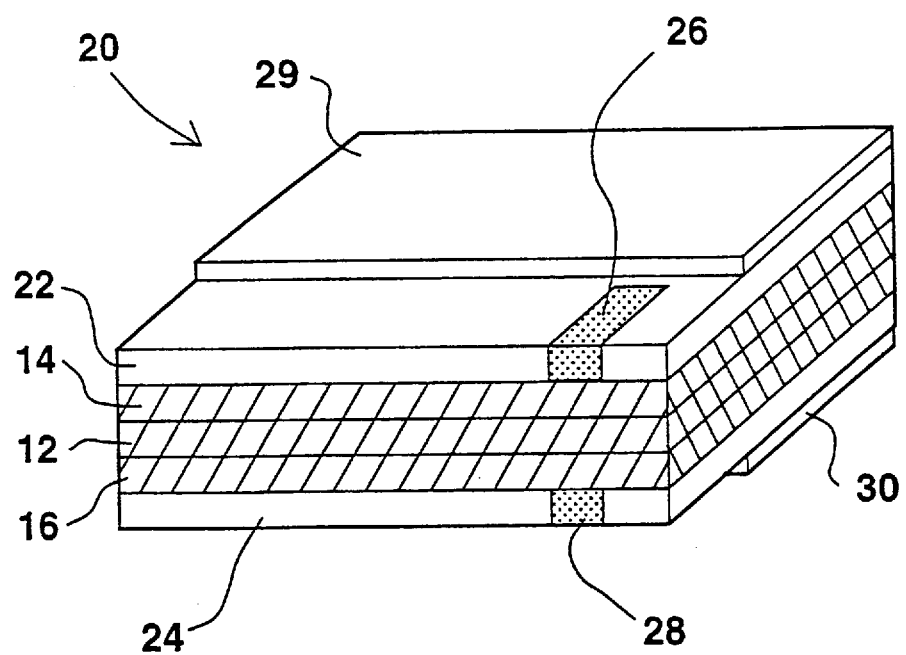
FIG. 2

FLEXIBLE THIN LAYER OPEN ELECTROCHEMICAL CELL

This is a continuation of application U.S. patent application Ser. No. 08/575,190, filed Dec. 20, 1995 now U.S. Pat. No. 5,652,043.

FIELD AND BACKGROUND OF THE INVENTION

The present invention relates to electrochemical cells which are used as battery power sources by converting chemical energy to electrical energy. More particularly, the present invention relates to a primary or rechargeable electrochemical cell to be used as a regular or rechargeable battery which accomplishes the conversion of chemical energy to electrical energy using a wet (e.g., liquid state) electrolyte, yet maintains a flexible thin layer and open configuration.

The ever-growing development of miniaturized and portable electrically powered devices of compact design such as, for example, cellular phones, voice recording and playing devices, watches, motion and still cameras, liquid crystal displays, electronic calculators, IC cards, temperature sensors, hearing aids, pressure sensitive buzzers, etc., generates an ever-growing need of compact thin layer batteries for their operation. Therefore, there is a need for reliable thin layer electrochemical cells to be used as batteries.

Batteries can be broadly classified into two categories in which the batteries of the first category include wet electrolytes (i.e., liquid state batteries), whereas batteries of the second category include solid state electrolytes. Although solid state batteries have an inherent advantage, they do not dry out and do not leak, they suffer major disadvantages when compared with liquid state batteries since, due to limited diffusion rates of ions through a solid, their operation is temperature dependent to a much larger extent, and many operate well only under elevated temperatures. And, the limited diffusion rates thus described characterize solid state batteries with low ratios of electrical energy generated vs. their potential chemical energy. Liquid state thin layer batteries typically include a positive and negative active insoluble material layer put together with a separator interposed therebetween, which separator is soaked with a liquid electrolyte solution, thus functioning as an electrolytic liquid layer. Such batteries, an example of which is disclosed in U.S. Pat. No. 4,623,598 to Waki et al., and in Japanese Pat. No. JP 61-55866 to Fuminobu et al., have to be sealed within a sheathing film to prevent liquid evaporation, and are therefore closed electrochemical cells. Being closed cells, these batteries tend to swell upon storage due to evolution of gases which is a fatal problem in thin layer batteries having no mechanical support. The pressure imposed by the accumulated gases leads to layer separation, thus turning the battery inoperative. Means to overcome this problem include (1) the use of a polymer increased viscosity agent, such as hydroxyethylcellulose, applied to adhere (i.e., glue) the battery layers together, to overcome the inherent problem of such batteries imposed by lack of solid support; and, (2) addition of mercury to prevent the formation of gases, especially hydrogen. However, the polymer is limited in its effectiveness and the mercury is environmental hazardous.

A way to solve the above described limitation was disclosed in U.S. Pat. No. 3,901,732 to Kis et al. in which a gas-permeable electrolyte-impermeable polymeric material which allows venting of undesirable gases formed within the battery while preventing any electrolyte loss from the battery is used as a sheathing film to enclose the battery cell.

However, a more direct and efficient way to avoid undesired gas accumulation in liquid state thin layer batteries would be to provide these batteries as open cells for facilitated release of gases, while at the same time to provide means to avoid liquid evaporation and drying out of the battery.

There is thus a widely recognized need for, and it would be highly advantageous to have, a flexible thin layer open electrochemical cell devoid of both accumulation of gases and liquid evaporation limitations.

SUMMARY OF THE INVENTION

According to the present invention there is provided a flexible thin layer open liquid state electrochemical cell which can be used as a primary or rechargeable power supply for various miniaturized and portable electrically powered devices of compact design. There is further provided a method of manufacturing such a cell. The flexible thin layer open electrochemical cell of the present invention includes a wet electrolyte, yet maintains a flexible, thin and open configuration, thus devoid of accumulation of gases upon storage.

According to further features in preferred embodiments of the invention described below, the cell comprising a first layer of insoluble negative pole, a second layer of insoluble positive pole and a third layer of aqueous electrolyte, the third layer being disposed between the first and second layers and including: (a) a deliquescent material for keeping the open cell wet at all times; (b) an electroactive soluble material for obtaining required ionic conductivity; and, (c) a watersoluble polymer for obtaining a required viscosity for adhering the first and second layers to the third layer.

According to still further features in the described preferred embodiments the electrolyte layer is engaged by a porous substance.

According to still further features in the described preferred embodiments the porous substance is selected from the group consisting of a filter paper, a plastic membrane, a cellulose membrane and a cloth.

According to still further features in the described preferred embodiments the first layer of insoluble positive pole includes manganese-dioxide powder and the second layer of insoluble negative pole includes zinc powder.

According to still further features in the described preferred embodiments the first layer of insoluble negative pole and/or the second layer of insoluble positive pole further includes carbon powder and the electroactive soluble material is selected from the group consisting of zinc-chloride, zinc-bromide, zinc-fluoride and potassium-hydroxide.

According to still further features in the described preferred embodiments the first layer of insoluble negative pole includes silver-oxide powder and the second layer of insoluble positive pole includes zinc powder and the electroactive soluble material is potassium-hydroxide.

According to still further features in the described preferred embodiments the first layer of insoluble negative pole includes cadmium powder and the second layer of insoluble positive pole includes nickel-oxide powder and the electroactive soluble material is potassium-hydroxide.

According to still further features in the described preferred embodiments the first layer of insoluble negative pole includes iron powder and the second layer of insoluble positive pole includes nickel-oxide powder and the electroactive soluble material is potassium-hydroxide.

According to still further features in the described preferred embodiments the first layer of insoluble negative pole and the second layer of insoluble positive pole include lead-oxide powder, the cell is charged by voltage applied to the poles and the electroactive soluble material is sulfuric-acid.

According to still further features in the described preferred embodiments the deliquescent material and the electroactive soluble material are the same material and are selected from the group consisting of zinc-chloride, zinc-bromide, zinc-fluoride and potassium-hydroxide.

According to still further features in the described preferred embodiments the deliquescent material is selected from the group consisting of calcium-chloride, calcium-bromide, potassium-biphosphate and potassium-acetate.

According to still further features in the described preferred embodiments the watersoluble polymer is selected from the group consisting of polyvinylalcohol, polyacrylamide, polyacrylic acid, polyvinylpyrolidone, polyethylenoxide, agar, agarose, starch, hydroxyethylcellulose and combinations and copolymers thereof.

According to still further features in the described preferred embodiments the watersoluble polymer and the deliquescent material are the same material and are selected from the group consisting of dextrane, dextranesulfate and combinations and copolymers thereof.

According to still further features in the described preferred embodiments the cell further comprising terminals, each of the terminals being in electrical contact with one of the first and second pole layers.

According to still further features in the described preferred embodiments the terminal are made of graphite or a metal.

According to still further features in the described preferred embodiments the metal is selected from the group consisting of iron, nickel, titanium, copper, stainless steel and mixtures thereof, and the terminals are applied to the cell by a suitable printing technology such as, but not limited to, silk print, offset print, jet printing, lamination, materials evaporation or powder dispersion.

According to still further features in the described preferred embodiments the cell further comprising at least one conductive layer improving the electronic conductivity of at least one of the first and second pole layers.

According to still further features in the described preferred embodiments the conductive layer is selected from the group consisting of a graphite paper and carbon cloth.

According to still further features in the described preferred embodiments the cell further comprising an external layer selected from the group consisting of an adhesive backing layer, a lamina protective layer and a combination of adhesive backing layer and a lamina protective layer.

According to still further features in the described preferred embodiments provided is an electrical power supply comprising at least two cells featured as above, the cells are connected in a head to tail orientation in a bipolar-connection.

According to still further features in the described preferred embodiments the connection is by an adhesive selected from the group consisting of a conductive double sided adhesive tape and a conductive glue layer.

According to still further features in the described preferred embodiments the conductive double sided adhesive tape and the conductive glue layer are applied by a printing technology.

According to still further features in the described preferred embodiments the cell comprising a first layer of insoluble negative pole, a second layer of insoluble positive pole and a third layer of aqueous electrolyte, the third layer being disposed between the first and second layers and including: (a) a watersoluble polymer for obtaining a required viscosity for adhering the first and second layers to the third layers and for obtaining a required hygroscopicality for keeping the open cell wet at all times; and (b) an electroactive soluble material for obtaining a required ionic conductivity.

According to still further features in the described preferred embodiments the method of making a flexible thin layer open liquid state electrochemical cell comprising the steps of (a) wetting a porous substance having a first side and a second side with an aqueous solution containing a deliquescent material, an electroactive soluble material and a watersoluble polymer; (b) applying onto the first side a layer of negative pole; and (c) applying onto the second side a layer of positive pole.

According to still further features in the described preferred embodiments the wetting is by a dipping or printing technologies.

According to still further features in the described preferred embodiments the layers of negative and positive poles include active insoluble powder materials mixed with the deliquescent material, electroactive soluble material and watersoluble polymer, the application of the layers of negative and positive poles is by a printing technology.

The present invention successfully addresses the shortcomings of the presently known configurations by providing a flexible thin layer open electrochemical cell which does not accumulate gases upon storage, yet it is maintained wet and intact by the use of a deliquescent material for keeping it wet at all times and a watersoluble polymer for obtaining the required viscosity for adhering the pole layers to the aqueous electrolyte layer. Further qualities of the cell include having no outer rigid casting therefore it is thin light and flexible and may be manufactured in any size, shape, color and applied patterns, hence it is suitable for a variety of applications; cost effectiveness; made of environmental and human friendly materials; and, self sticking via an adhesive backing.

BRIEF DESCRIPTION OF THE DRAWINGS

The invention herein described, by way of example only, with reference to the accompanying drawings, wherein:

FIG. 1 is a perspective view of a basic configuration of a flexible thin layer open electrochemical cell according to the teachings of the present invention;

FIG. 2 is a is a perspective view of another possible configuration of a flexible thin layer open electrochemical cell;

DESCRIPTION OF THE PREFERRED EMBODIMENTS

Figure 3A:
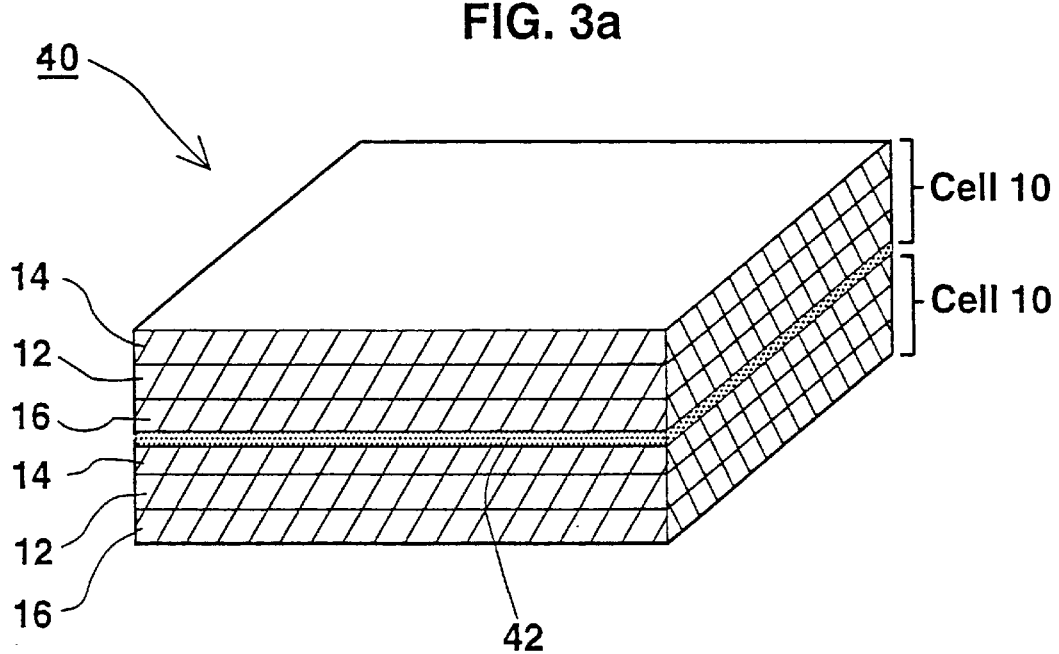
FIGS. 3a and 3b are perspective views of two possible configurations of power supplies formed by a a bi-polar connection of two cells of FIG. 1 and FIG. 2, respectively, to additively increase the electrical energy obtained of thus formed electrical power supplies.

The present invention is of a flexible thin layer open electrochemical cell which can be used as a primary or rechargeable power supply for various miniaturized and portable electrically powered devices of compact design. The flexible thin layer open electrochemical cell of the present invention includes a wet electrolyte, yet maintains a flexible, thin and open configuration, thus devoid of accumulation of gases upon storage.

The principles and operation of a flexible thin layer open electrochemical cell according to the present invention may be better understood with reference to the drawings and accompanying descriptions.

Referring now to the drawings, FIG. 1 illustrates a basic configuration of the flexible thin layer open electrochemical cell of the present invention, generally designated 10. Cell 10 includes three layers as follows. A first layer of insoluble negative pole 14, a second layer of insoluble positive pole 16 and a third layer of aqueous electrolyte 12. As used in this document, on discharged negative pole is where an oxidation occurs, whereas the positive pole is where reduction occurs. The aqueous electrolyte layer 12 includes a deliquescent (i.e., hygroscopic) material for keeping open cell 10 wet at all times; an electroactive soluble material for obtaining the required ionic conductivity; and a watersoluble polymer for obtaining the required viscosity for adhering pole layers 14 and 16 to aqueous electrolyte layer 12. Following is a more detailed description of each of layers 14, 16 and 12 and their role in open cell 10 operation.

The aqueous electrolyte layer 12 typically includes a porous insoluble substance, such as but not limited to, filter paper, plastic membrane, cellulose membrane, cloth, etc., the porous substance is wetted by an aqueous solution including three components: a deliquescent material; an electroactive soluble material; and a watersoluble polymer.

The deliquescent material by being hygroscopic maintains cell 10 moisturized at all times. The level of moisture within open cell 10 may vary depending on deliquescent material selection, its concentration and air humidity. Suitable deliquescent materials include, but are not limited to, calcium-chloride, calcium-bromide, potassium-biphosphate, potassium-acetate and combinations thereof.

The electroactive soluble material is selected in accordance with the materials of which the negative and positive pole layers are made. A list of frequently used electroactive soluble materials suitable for the present invention includes for example zinc-chloride, zinc-bromide and zinc-fluoride for various primary cells and potassium-hydroxide and sulfuric-acid for rechargeable cells.

The watersoluble polymer is employed as an adhesive agent to adhere (i.e., glue) pole layers 14 and 16 to the aqueous electrolyte layer 12. Many types of polymers are suitable ones, such as for example polyvinylalcohol, polyacrylamide, polyacrylic acid, polyvinylpyrolidone, polyethylenoxide, agar, agarose, starch, hydroxyethylcellulose and combinations and copolymers thereof.

Each of negative and positive pole layers 14 and 16 includes a mix of a suitable (negative or positive, respectively) active insoluble powder material with an aqueous solution similar to the solution described hereinabove, including a deliquescent material; an electroactive soluble material; and a watersoluble polymer.

It is clear to those with skills in the art that while the electroactive soluble material should not change, the deliquescent material and the watersoluble polymer may be selected otherwise in the later solution, in other words, the electroactive soluble material should be kept the same in all three layers 12, 14 and 16, whereas the deliquescent material and the watersoluble polymer may be varied between layers according to the specific application.

Appropriate selection of active insoluble powder materials for the negative 14 and positive 16 pole layers with a matching electroactive soluble material, as exemplified hereinbelow in the Examples, provides flexible thin layer cell 10 which can be used as a power supply (i.e., a battery), which cell 10 is open and therefore does not accumulate gases upon storage, yet the hygroscopicality of the deliquescent material ensures that cell 10 is kept wet at all times although open. Suitable pairs of materials to be used in negative 14 and positive 16 poles include, but are not limited to, manganese-dioxide/zinc; silver-oxide/zinc; cadmium/nickel-oxide; and iron/nickel-oxide (the manganese-dioxide and the silver-oxide are optionally mixed with a conductive carbon powder as known in the art).

It is clear to those with skills in the art that a single material may function both as a deliquescent material and as the electroactive soluble material. Such a material should however acquire suitable electroactive and hygroscopic characteristics. Suitable materials of this type include, but are not limited to, zinc-chloride and zinc-bromide.

It is further clear to those with skills in the art that a single material may function as a deliquescent material and as a watersoluble polymer. Such a material should however acquire suitable hygroscopic adhesivness characteristics. Suitable materials of this type include, but are not limited to, dextrane, dextranesulfate and combinations and copolymers thereof.

The three layers 12, 14 and 16, presented in FIG. 1 and described hereinabove may be manufactured thin and are flexible, therefore cell 10 is flexible and as thin as 0.5–1.5 mm or less. It is presently preferred and will be further detailed below that cell 10 will be manufactured by a suitable printing technology. Suitable printing technologies include, but are not limited to, silk print, offset print, jet printing, lamination, materials evaporation and powder dispersion.

Another possible configuration is shown in FIG. 2 illustrating a cell, generally assigned 20. As cell 10, cell 20 also includes layers 12, 14 and 16 (stripped region) forming a basic cell. Cell 20 further includes additional one or two conductive layers 22 and 24, to improve the electronic conductivity of negative 14 and/or positive 16 pole layers. Suitable conductive layers are graphite paper, carbon cloth, etc. Cell 20 also includes negative 26 and positive 28 terminals, which terminals 26 and 28 are in electrical contact with either the corresponding pole layer 14 and 16, respectively, or with the corresponding conductive layer 22 and 24, respectively, or both. Terminals 26 and 28 are made of any suitable materials such as, but not limited to, graphite or metals such as iron, nickel, titanium, copper, stainless steel and mixtures thereof, and are preferably applied to cell 20 by a suitable printing technology such as the ones listed above. Terminals 26 and 28 are used to electrically connect cell 20 to a load such as an electrically powered device. Terminals 26 and 28 may be located in any desired location of cell 20, may acquire any suitable shape and size and, depending on the specific application, terminals 26 and 28 may protrude from the surface of cell 20. Cell 20 may further include at least one externally located adhesive backing 29, to enable attaching cell 20 to various surfaces, and/or at least one externally located lamina protective layer 30 to physically protect all other layers.

Figure 3B:
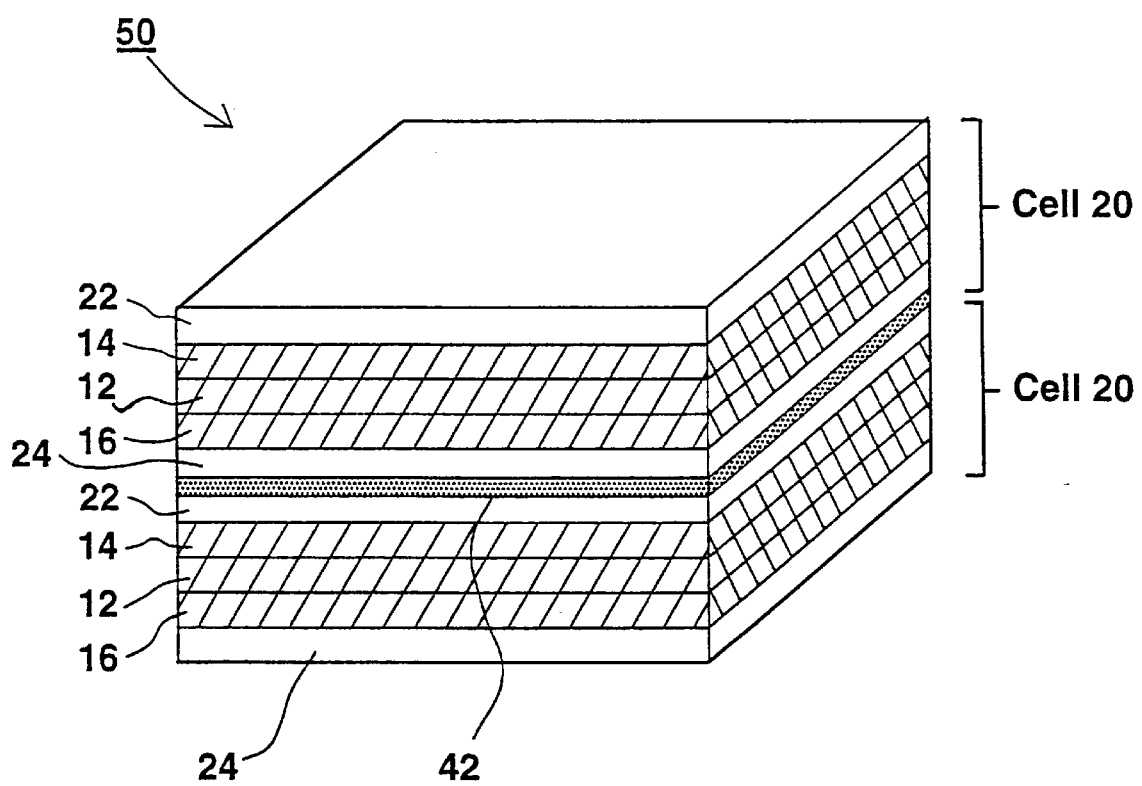

Yet another configuration is shown in FIGS. 3a–b. Two or more cells 10, as shown in FIG. 3a, or cells 20, as shown in FIG. 3b, may be electrically connected by a bi-polar connection to additively increase the electrical energy obtained of thus formed electrical power supplies 40 and 50, respectively. For this purpose two or more cells are adhered to one another in a head to tail orientation, as indicated in FIGS. 3a–b by layers 22, 14, 12, 16 and 24 arrangement, by a conductive double sided adhesive tape, or a conductive glue layer 42 applied for example by a suitable printing technology, enabling passage of electrons between adjacent cells. It is clear that electrical power supplies 40 and/or 50 may further include externally located adhesive backing(s) similar to surface 29 of FIG. 2 and/or externally located lamina protective layer(s), similar to layer 30 of FIG. 2. It is further clear that electrical power supplies 40 and 50 may include a negative and a positive terminal similar to terminals 26 and 28, respectively, of FIG. 2.

The present invention further includes a method of making a flexible thin layer open liquid state electrochemical cells similar to the cells described above, the method includes the steps of (a) wetting a porous substance an aqueous solution containing a deliquescent material, an electroactive soluble material and a watersoluble polymer; wetting may be achieved by either dipping or printing technologies; (b) applying onto one side of the porous substance a negative pole layer; and, (c) applying onto the second side of the porous substance a positive pole layer. The negative and positive pole layers include active insoluble powder substances mixed with the deliquescent material, electroactive soluble material and watersoluble polymer preferably of the same types as under (a), and are preferably applied using a suitable printing technology selected for example from the ones listed above.

The method may further include adding to the cell additional layers and parts, such as but not limited to, externally located adhesive backing(s) and/or lamina protective layer (s), and negative and a positive terminals. Yet, the method may further include bi-polar joining of two or more cells, for example with a conductive double sided adhesive tape or a conductive glue layer applied for example by a suitable printing technology, to form a power supply with an increased power (e.g., substantially doubled, tripled, etc.). According to the present invention such bi-polar joining may be performed by joining together in a head to tail orientation two or more premanufactured cells, or alternatively, directly manufacturing two or more cells thus oriented, by applying suitable layer one after the other, preferably using a suitable printing technology as described above.

The flexible thin layer open electrochemical cell of the present invention has a major advantage over prior art thin layer cells. Since it is an open cell it does not accumulate gases upon storage, yet it is maintained wet and intact by the use of a deliquescent material for keeping it wet at all times and a watersoluble polymer for obtaining the required viscosity for adhering the pole layers to the aqueous electrolyte layer.

The flexible thin layer open electrochemical cell of the present invention has other qualities as follows. First, it has no outer rigid casting therefore it is thin light and flexible and may be manufactured in any size, shape, color and applied patterns, hence it is suitable for a variety of applications. Second, by using a suitable printing technology for its manufacturing its cost is reduced and therefore it may be disposed after use partly since large sheets can be produced and cut to any desired size following printing and partly since this technology is inherently cost effective. Third, it is preferably made of environmental and human friendly materials (it preferably contains no mercury or heavy metals). And finally, it may be manufactured self sticking via an adhesive backing.

Reference in now made to the following examples, which together with the above descriptions, illustrate the invention.

EXAMPLE 1

A solution containing 120 mg of polyvinylalcohol (an aqueous soluble polymer) and 1680 mg of zinc-chloride (a deliquescent material and an electroactive soluble material) in 1.2 ml of water was prepared. This solution had a glue like viscous appearance. A 4.5 cm×7 cm strip of a filter paper was thoroughly wetted with this solution by a printing or dipping technologies. A mixture of 300 mg zinc powder with the above solution was prepared and was printed on one side of the paper strip serving as the negative pole layer. On the other side printed was a mixture of 250 mg manganese-dioxide and 50 mg of a conductive carbon powder, together with the above solution, serving as the positive pole layer. When electrical contacts were made with both sides and were connected over a load an electrical current was measured. A current of 12 microampers per $cm^2$ at a voltage of 1.7÷1.2 volts was easily maintained for five days continuously under room conditions.

EXAMPLE 2

Figure 4:
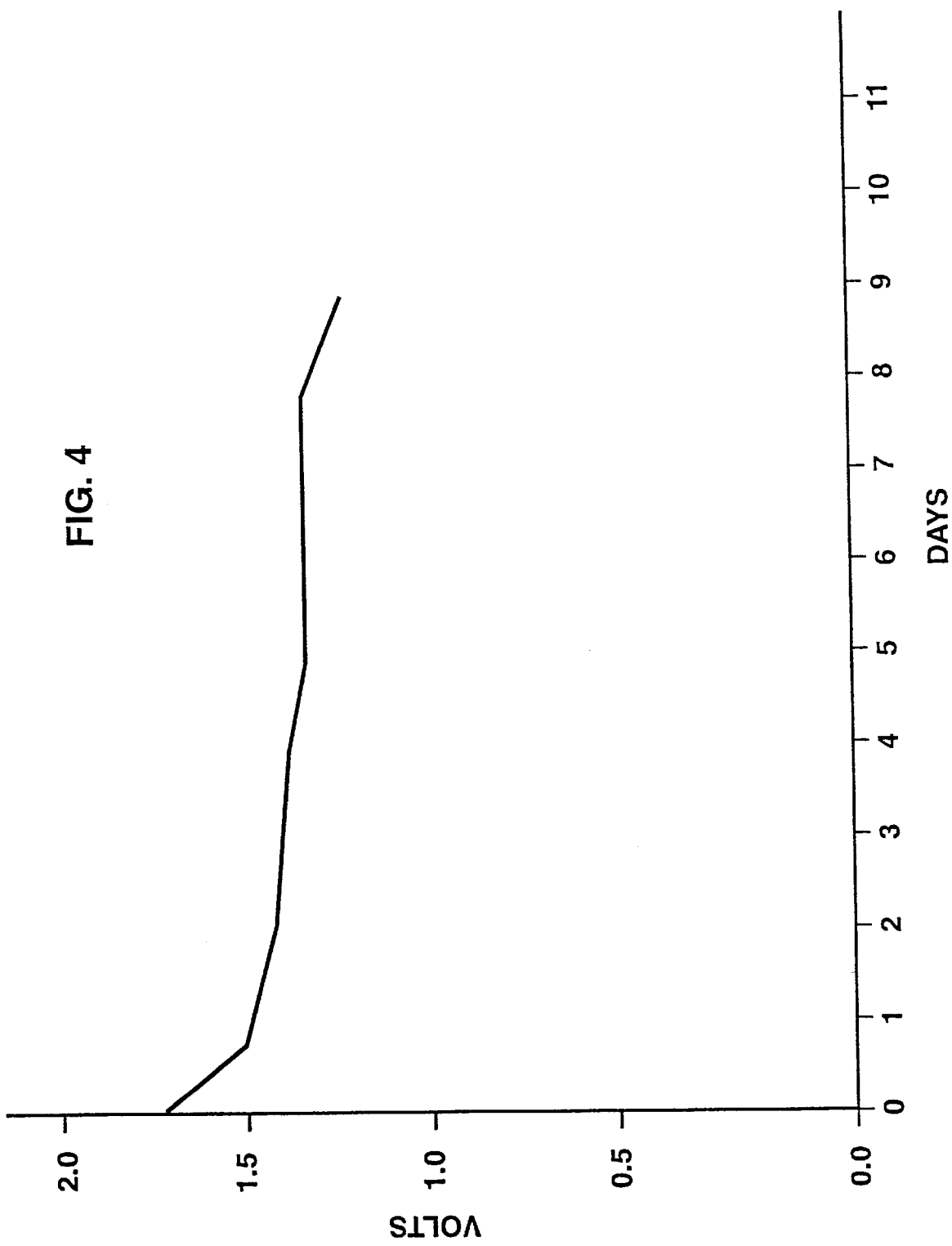
FIG. 4 is a graph presenting the voltage of a flexible thin layer open electrochemical cell according to the present invention, as measured by a voltmeter, as function of time, under room conditions.

An open cell was prepared as described under Example 1 above and was connected to a voltmeter. As shown in FIG. 4, measurement of the voltage produced by the cell under room conditions revealed a pronounced voltage of 1.7÷1.2 sustained for nine successive days.

EXAMPLE 3

A saturated potassium-hydroxide solution is prepared and brought to the viscosity of a glue by mixing with a water soluble polymer. A porous substance (e.g., a filter paper) is thoroughly wetted with this solution and a mixture of the solution with nickel-oxide powder is pasted on one side of the porous substance to form a positive pole layer and, a similar mixture with cadmium powder is pasted on the other side of the porous substance to form a negative pole layer. By connecting a voltmeter to the two sides a voltage of 1.2 volts is measured and a high current is measured when the two layers are contacted over a load. The cell does not dry out in the open and can be recharged if so desired.

EXAMPLE 4

The same potassium-hydroxide solution as in Example 3 is prepared and a porous substance is wetted with it. A mixture of the solution with zinc powder is pasted on one side of the porous substance to form a negative pole layer and a similar mixture with silver-oxide powder containing some carbon powder if so desired is pasted on the other side of the porous substance to form a positive pole layer. By connecting a voltmeter to the two sides a voltage of 1.2 volts is measured and appreciable current is measured when the two layers are contacted over a load. The cell does not dry out in the open and can be recharged if so desired.

EXAMPLE 5

The same potassium-hydroxide solution as in Example 3 is prepared and a porous substance is wetted with it. A mixture of the solution with zinc powder is pasted on one side of the porous substance to form a negative pole layer and a similar mixture with manganese-dioxide powder containing some carbon powder if so desired is pasted on the other side of the porous substance to form a positive pole layer. By connecting a voltmeter to the two sides a voltage of 1.5 volts is measured and appreciable current is measured when the two layers are contacted over a load. The cell does not dry out in the open. Recharging thus formed cell may be troublesome.

EXAMPLE 6

The same potassium-hydroxide solution as in Example 3 is prepared and a porous substance is wetted with it. A mixture of the solution with nickel-oxide powder is pasted on one side of the porous substance to form a positive pole layer and a similar mixture with iron powder is pasted on the other side of the porous substance to form a negative pole layer. By connecting a voltmeter to the two sides a voltage of 0.9 volts is measured and a current can be measured when the two layers are contacted over a load. The cell does not dry out in the open and some recharged is possible if so desired.

EXAMPLE 7

A 30% sulfuric acid solution is prepared and brought to the viscosity of a glue by mixing with a water soluble polymer. A porous substance (e.g., a filter paper) is thoroughly wetted with this solution and a mixture of the solution with lead-oxide is pasted on both sides of the porous substance. Both sides are connected to a power supply and a voltage higher than 2 volts is applied by which the cell is charged. Charge and discharge cycles can be repeated without the cell drying out in the open.

While the invention has been described with respect to a limited number of embodiments, it will be appreciated that many variations, modifications and other applications of the invention may be made.

What is claimed is:

1. A flexible thin layer open liquid state electrochemical cell comprising a first layer of insoluble negative pole, a second layer of insoluble positive pole and a third layer of aqueous electrolyte, said third layer being disposed between said first and second layers and including:
   (a) a deliquescent material for keeping the open cell wet at all times;
   (b) an electroactive soluble material for obtaining required ionic conductivity; and
   (c) a watersoluble polymer for obtaining a required viscosity for adhering said first and second layers to said third layer.

2. A cell as in claim 1, wherein said first layer of insoluble positive pole includes manganese-dioxide powder and said second layer of insoluble negative pole includes zinc powder.

3. A cell as in claim 2, wherein said electroactive soluble material is selected from the group consisting of zinc-chloride, zinc-bromide, zinc-fluoride and potassium-hydroxide.

4. A cell as in claim 1, wherein said first layer of insoluble negative pole includes silver-oxide powder and said second layer of insoluble positive pole includes zinc powder.

5. A cell as in claim 4, wherein said electroactive soluble material is potassium-hydroxide.

6. A cell as in claim 1, wherein said first layer of insoluble negative pole includes cadmium powder and said second layer of insoluble positive pole includes nickel-oxide powder.

7. A cell as in claim 6, wherein said electroactive soluble material is potassium-hydroxide.

8. A cell as in claim 1, wherein said first layer of insoluble negative pole includes iron powder and said second layer of insoluble positive pole includes nickel-oxide powder.

9. A cell as in claim 8, wherein said electroactive soluble material is potassium-hydroxide.

10. A cell as in claim 1, wherein said first layer of insoluble negative pole and said second layer of insoluble positive pole include lead-oxide powder, the cell is charged by voltage applied to said poles.

11. A cell as in claim 10, wherein said electroactive soluble material is sulfuric-acid.

12. A cell as in claim 1, wherein said deliquescent material and said electroactive soluble material are the same material.

13. A cell as in claim 12, wherein said same material is selected from the group consisting of zinc-chloride, zinc-bromide, zinc-fluoride and potassium-hydroxide.

14. A cell as in claim 1, wherein said deliquescent material is selected from the group consisting of calcium-chloride, calcium-bromide, potassium-biphosphate and potassium-acetate.

15. A cell as in claim 1, wherein said watersoluble polymer is selected from the group consisting of polyvinylalcohol, polyacrylamide, polyacrylic acid, polyvinylpyrolidone, polyethylenoxide, agar, agarose, starch, hydroxyethylcellulose and combinations and copolymers thereof.

16. A cell as in claim 1, wherein said watersoluble polymer and said deliquescent material are the same material.

17. A cell as in claim 1, wherein said same material is selected from the group consisting of dextrane, dextrane-sulfate and combinations and copolymers thereof.

18. A cell as in claim 1, further comprising terminals, each of said terminals being in electrical contact with one of said first and second pole layers.

19. A cell as in claim 18, wherein said terminal are made of graphite.

20. A cell as in claim 1, further comprising at least one conductive layer improving the electronic conductivity of at least one of said first and second pole layers.

21. A cell as in claim 20, wherein said conductive layer is selected from the group consisting of a graphite paper and carbon cloth.

22. A cell as in claim 1, further comprising an external layer selected from the group consisting of an adhesive backing layer, a lamina protective layer and a combination of adhesive backing layer and a lamina protective layer.

23. An electrical power supply comprising two cells as in claim 1 being connected in a head to tail orientation in a bipolar-connection.

24. An electrical power supply as in claim 23, wherein said connection is by an adhesive selected from the group consisting of a conductive double sided adhesive tape and a conductive glue layer.

25. An electrical power supply as in claim 24, wherein said conductive double sided adhesive tape and said conductive glue layer are applied by a printing technology.

26. A method of making a flexible thin layer open liquid state electrochemical cell comprising the steps of:
   (a) wetting a porous substance having a first side and a second side with an aqueous solution containing a deliquescent material, an electroactive soluble material and a watersoluble polymer;
   (b) applying onto said first side a layer of negative pole; and
   (c) applying onto said second side a layer of positive pole.

27. A method as in claim 26, wherein said wetting is by a dipping technology.

28. A method as in claim 26, wherein said wetting is by a printing technology.

29. A method as in claim 26, wherein said layers of negative and positive poles include active insoluble powder materials mixed with said deliquescent material, electroactive soluble material and watersoluble polymer.

30. A method as in claim 26, wherein said application of said layers of negative and positive poles is by a printing technology.

* * * * *